United States Patent [19]

Larsson et al.

[11] Patent Number: 5,540,233

[45] Date of Patent: Jul. 30, 1996

[54] METHOD FOR DETERMINING THE FUNCTIONAL RESIDUAL CAPACITY OF LUNGS AND A VENTILATOR FOR PRACTICING SAID METHOD

[75] Inventors: Anders Larsson, Kaevlinge; Rolf Castor, Haegerstein; Stefan Brauer, Soedra Sandby; Sven G. Olsson, Arloev, all of Sweden

[73] Assignee: Siemens-Elema AB, Solna, Sweden

[21] Appl. No.: 327,990

[22] Filed: Oct. 24, 1994

[30] Foreign Application Priority Data

Oct. 22, 1993 [SE] Sweden ................................ 9303486

[51] Int. Cl.⁶ .................................................. A61B 5/091
[52] U.S. Cl. ................................... 128/725; 128/719
[58] Field of Search ..................................... 128/716, 719, 128/725

[56] References Cited

U.S. PATENT DOCUMENTS

| | | |
|---|---|---|
| 3,527,206 | 9/1970 | Jones . |
| 3,659,590 | 5/1972 | Jones et al. . |
| 3,785,370 | 1/1974 | Richards et al. ........................ 128/719 |
| 4,418,701 | 12/1983 | Luijpers . |
| 4,941,476 | 7/1990 | Fisher ....................................... 128/719 |

FOREIGN PATENT DOCUMENTS

| | | | |
|---|---|---|---|
| 2692772 | 12/1993 | France .................................... 128/725 |
| 2698260 | 5/1994 | France .................................... 128/725 |
| 952212 | 8/1982 | U.S.S.R. ................................. 128/725 |

OTHER PUBLICATIONS

"Measurement of Functional Residual Capacity by Sulfur Hexafluoride Washout," Jonmarker, University of Lund, Sweden, 1985.

*Primary Examiner*—Lee S. Cohen
*Attorney, Agent, or Firm*—Hill, Steadman & Simpson

[57] ABSTRACT

In a method and a ventilator device for measuring the functional residual capacity, FRC, of lungs, a trace gas is mixed with a breathing gas in a gas mixer and the mixture os fed into the lungs via an inspiratory tube. When a predetermined concentration of trace gas is achieved in the lungs, the supply of trace gas is stopped, and a washout phase starts. During the washout phase, the concentration of trace gas in expired gas and the flow of expired gas are measured. The measurement values are sent to an analyzer which calculates the volume of trace gas in the lungs. Functional residual capacity can then be determined from the calculated volume of trace gas. The trace gas is preferably $SF_6$.

7 Claims, 2 Drawing Sheets

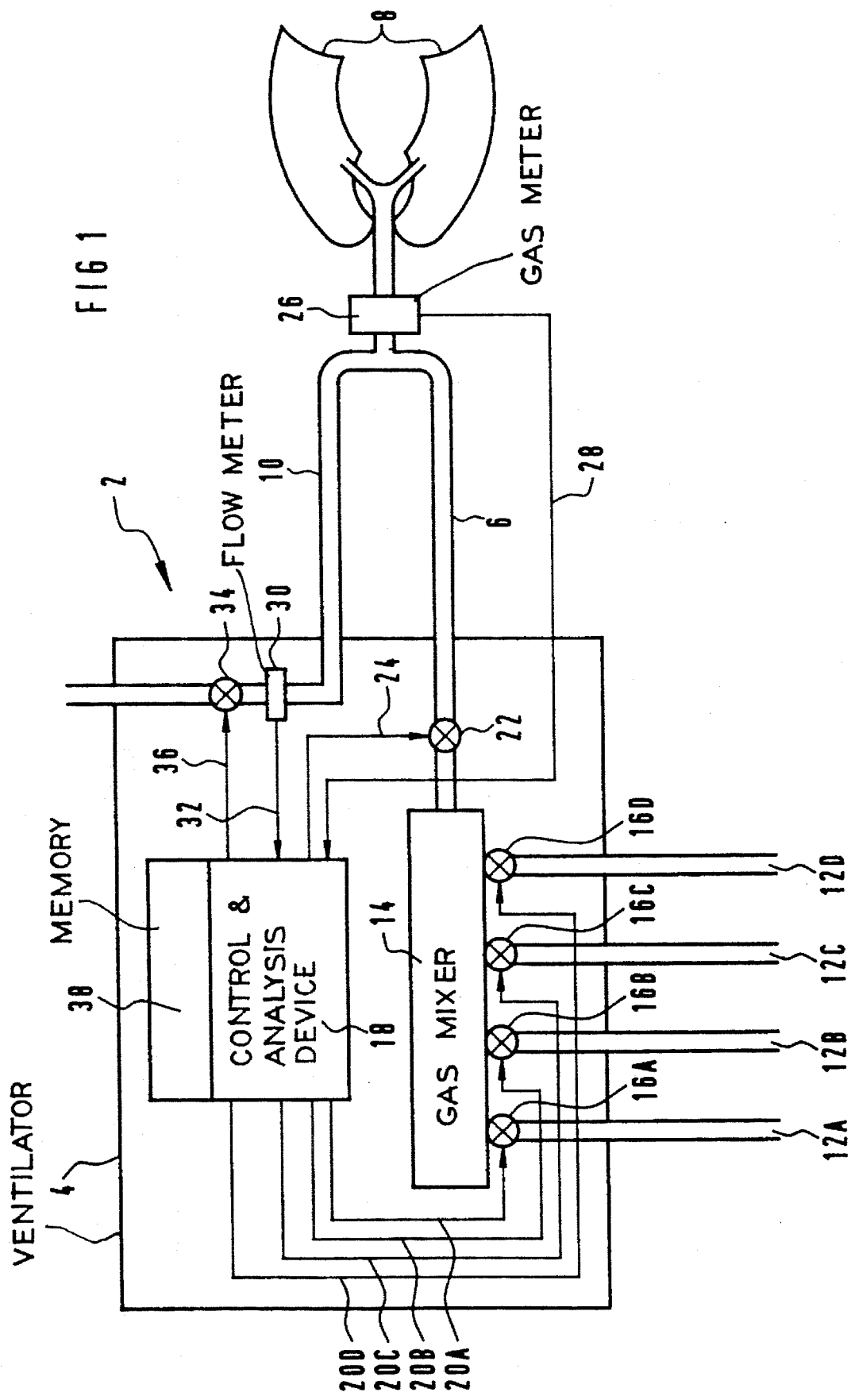

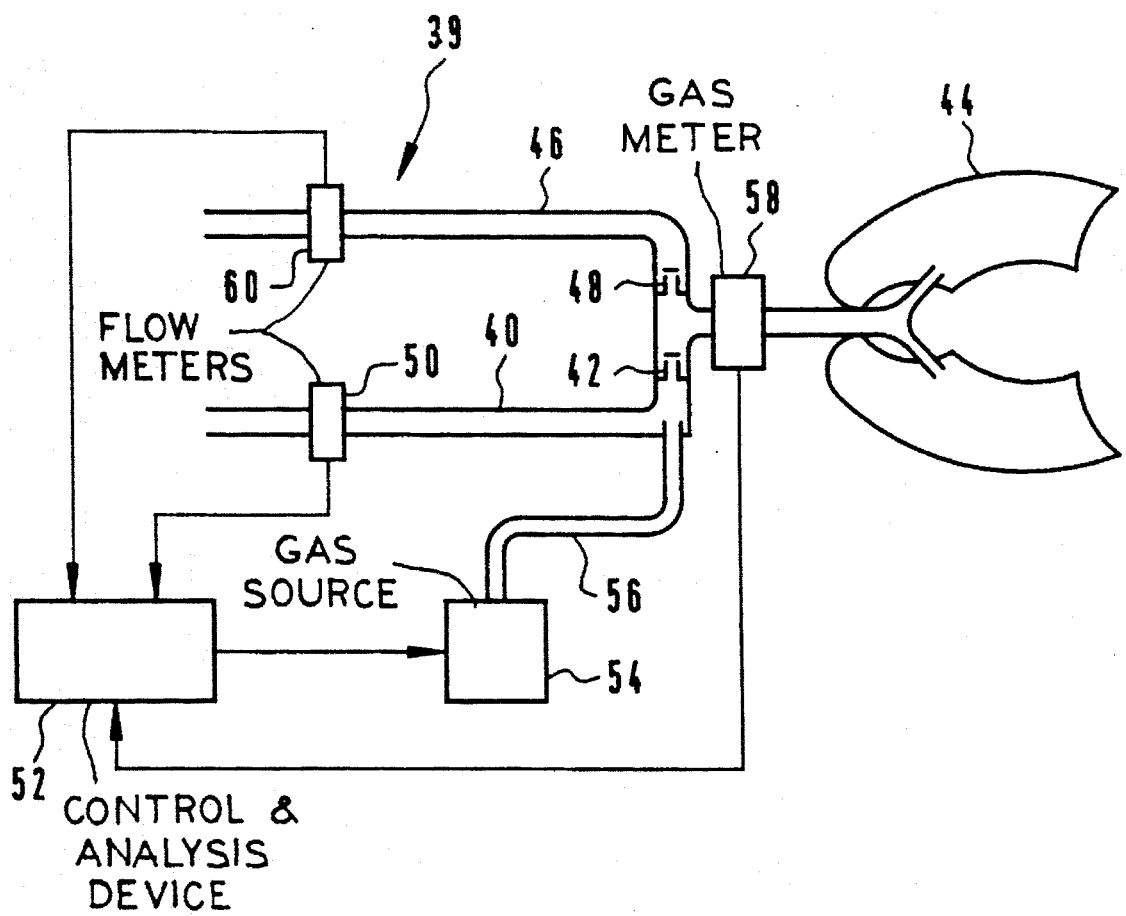

METHOD FOR DETERMINING THE FUNCTIONAL RESIDUAL CAPACITY OF LUNGS AND A VENTILATOR FOR PRACTICING SAID METHOD

BACKGROUND OF THE INVENTION

1. Field of the Invention

The present invention relates to a method by determination of the functional residual capacity (FRC) of lungs, and to a ventilator device for the determination of the functional residual capacity.

2. Description of the Prior Art

The functional residual capacity is the volume of gas remaining in the lungs and airways at the end of a normal expiration. This gas volume serves, inter alia, as a reservoir of oxygen for the body. A reduction in FRC affects a number of functions in the respiratory organs, such as airway resistance, lung compliance, the distribution of inspired gas and arterial oxygenation. It is therefore an advantage if FRC can be measured in a simple way as one step in diagnosing a patient. Measurement of FRC is also useful during anaesthesia, since the administration of an anaesthetic reduces FRC.

One way of measuring FRC is described in a doctoral thesis entitled "Measurement of Functional Residual Capacity by Sulphur Hexafluoride Washout" (pp. 11–15) by C. Jonmarker, Dept. of Anaesthesia and Clinical Physiology, University of Lund, Lund 1985. An inert, non-toxic trace gas (sulphur hexafluoride, $SF_6$), is fed into the lungs of a patient during a wash-in phase. The gas is supplied directly to the lungs through a tracheal tube arranged after a gas meter. The gas meter measures the concentration of $SF_6$ in gas expired from the lungs. After a number of respiratory cycles, an equilibrium will arise, in which the concentration of $SF_6$ in the lungs is the same as the concentration of $SF_6$ supplied in the inspired gas, e.g. 0.5%, which is less than the hygienic limit value for $SF_6$. A washout phase, in which the administration of $SF_6$ is stopped, is then begun, and the lungs are gradually emptied of $SF_6$. During this washout phase, the concentration of $SF_6$ in the expired gas and the flow of expired gas are measured. The washout phase continues until the concentration drops below a defined level, e.g. 0.01%. The total volume of $SF_6$ washed out of the lungs is then calculated from the values measured for concentration and flow. A correction is made to compensate for the re-breathing of a certain amount of gas in the transition from expiration to inspiration. FRC is then calculated as the volume of $SF_6$ divided by the concentration of $SF_6$ at the end of the wash-in phase. This concentration is regarded as the concentration in the alveoli. During the actual measurement, the gas meter is periodically zeroed during the inspiratory phases. As a rule, the gas meter is calibrated with a test gas before the system is connected to a patient.

FRC can also be determined using helium, He, or nitrogen ($N_2$), as the trace gas.

In the known method and equipment, a breathing gas is supplied by a ventilator, and the trace gas is supplied by a separate gas source. This means that a number of units must be interconnected when an FRC measurement is to be made. The separate supply of trace gas also means that the trace gas and the breathing gas might not mix completely before being fed into the lungs. Furthermore, the gas meter is calibrated with a test gas before the; equipment is set up. Disruptions thus could affect the calibration before measurements are made. A conventional IR gas meter is often used when $SF_6$ is the trace gas. A cuvette is then irradiated with IR light, and absorption is measured at a specific wavelength. The meter is calibrated with clean cuvette windows, but the windows may have become slightly soiled at the time FRC measurement begins. This would affect the measurement and result in an erroneous reading.

SUMMARY OF THE INVENTION

An object of the invention is to provide a method for measuring FRC which is easy to perform and which supplies accurate, reliable results.

Another object of the invention is to provide a ventilator device capable of easily performing the method and calculating FRC without the need for connection of any additional units to the ventilator unit and without the soiling of cuvette windows, etc. being able to affect results.

In one embodiment of a method in accordance with the invention a breathing gas comprising a predetermined concentration of a trace gas is fed into the lungs via a gas meter during a wash-in phase, and the concentration of trace gas in gas inspired by and expired from the lungs is measured with the gas meter. The feeding of trace gas into the lungs is stopped after the concentration of trace gas measured in expired gas becomes identical to the concentration of trace gas measured in inspired gas, and a washout phase is started, during which the concentration of trace gas in the expired gas is measured with the gas meter until the measured concentration drops below a predetermined threshold value. The flow of expired gas is measured for every respiratory cycle in the washout phase and the volume of expired trace gas is calculated from the measured concentration and the measured flow of gas.

Supplying the trace gas mixed with the breathing gas makes possible an even distribution of trace gas in the lungs. This means, however, that the gas meter cannot be zeroed during the wash-in phase, since trace gas would also be passing the meter at this time. This could be viewed as a disadvantage of the method, but it can instead be employed as an advantage in FRC calculations. When no $SF_6$ is supplied, a measurement signal for 0% $SF_6$ is obtained. When an exact concentration of trace gas is then added to the breathing gas and the concentration of trace gas is measured during both inspiration and expiration during wash-in, the gas meter can be calibrated at the known, exact concentration of trace gas before the washout phase starts. The gas meter will then be calibrated at a time which is much closer to the measurement point in time than if the calibration had been performed earlier with a test gas. Moreover, calibration is performed under the actual measurement conditions. The influence of, e.g., cuvette soiling etc. will not affect the measurement as much as when the calibration is performed earlier.

In the determination of a null level for the concentration, a level can advantageously be set at the predetermined concentration. The measurement signal from the gas meter only indicates a voltage level, and a null level for this voltage can be set at any desired point, e.g., at the predetermined concentration.

In order to correct measurements for the gas meter's signal drift, preferably the measurement values during the washout phase are stored in a memory, and the gas meter's signal drift is measured and the measurement values are corrected for the measured signal drift before volume is calculated. The signal drift can be measured during inspiration in the washout phase when the concentration of $SF_6$ in inspired gas is 0%. Any difference in the measurement signal between breaths is then mainly due to signal drift.

FRC can be calculated more rapidly if the wash-in/washout curve is mathematically adapted before it terminates.

In order to correct for re-breathed gas, it is advantageous if the trace gas in inspired gas is measured during the washout phase, the volume of re-breathed trace gas is determined and the calculated volume is corrected for the re-breathed volume of trace gas. The true volume, rather than the estimated volume, of re-breathed trace gas is calculated. This can be performed in at least two different ways. One way is to estimate the volume which is re-breathed, assume that this volume is constant in each respiratory cycle, measure the concentration of trace gas in re-breathed gas and calculate the volume of re-breathed gas. A second way is to measure the flow of re-breathed gas and concentration of trace gas and calculate the volume of re-breathed trace gas. The second method yields a more accurate value.

In another embodiment of the method in accordance with the invention a breathing gas comprising a predetermined concentration of a trace gas is fed into the lungs via a gas meter during a wash-in phase, and the concentration of trace gas in the gas inspired by and expired from lungs is measured with the gas meter during the wash-in phase until the concentration of trace gas in inspired gas is equal to the concentration of trace gas in expired gas. The flow of inspired gas is measured for each respiratory cycle during the wash-in phase, the flow of expired gas is measured for every respiratory cycle in the wash-in phase, and the volume of inspired and expired trace gas respectively in the wash-in phase are calculated from the measured concentrations and gas flows. The volume of trace gas in the lungs is determined by subtracting the volume of trace gas expired from the lungs from the volume of inspired trace gas.

Determination of trace gas volumes in the wash-in phase make calculation of the volume of residual trace gas in the lungs and, thus, FRC, easy. Measurement points for calibration are achieved before trace gas is added (0%) and when equilibrium has developed (the predetermined concentration). Signal drift can be determined with measurements made after the supply of trace gas has stopped (0%). The volume of re-breathed trace gas can be determined in the same way as in the first embodiment. In both embodiments, determination of the volume of re-breathed trace gas can be simplified if check valves are installed in the gas lines to and from the patient. The check valves allow gas to flow only in one direction.

Both embodiments can also be used with conscious, spontaneously breathing patients as well as with unconscious patients whose breathing is fully controlled by a ventilator device.

In some instances, a positive end-expiratory pressure, PEEP, is used. A change in PEEP during wash-in or washout can change the time constant for the washin/washout curve. This would supply useful information for setting PEEP and calculating FRC.

A ventilator device is achieved in accordance with the invention including an analyzer for determining the functional residual capacity, FRC, of lungs, a ventilator unit for supplying and carrying away breathing gas to/from the lungs, a gas source for supplying a trace gas to the lungs, during a wash-in phase, in the inspiration phase for a number of respiratory cycles until the lungs contain a predetermined concentration of the trace gas, a gas meter for measuring the concentration of the trace gas, during the wash-in phase and a washout phase, in the expiration phase for a number of respiratory cycles until the concentration measured during the washout phase falls below a predetermined threshold value and a flow meter for measuring the flow of expired gas during the washout phase. The values measured for concentration and flow during the washout phase are supplied to the analyzer for determination of the volume of trace gas leaving the lungs and FRC. The gas source is connected to the ventilator unit in which the breathing gas and the trace gas are mixed before being supplied to the lungs, whereupon both the breathing gas and the trace gas pass the gas meter.

An improvement of the ventilator device is achieved in an embodiment of the invention wherein tile analyzer has a memory in which measurement values for the concentration of the trace gas and the flow of expired gas are stored during the washout phase.

DESCRIPTION OF THE DRAWINGS

FIG. 1 shows one embodiment of the ventilator device according to the invention.

FIG. 2 shows another apparatus capable of performing the method according to the invention.

DESCRIPTION OF THE PREFERRED EMBODIMENTS

The ventilator apparatus 2 in FIG. 1 includes a ventilator 4 which can supply a gas mixture to a pair of lungs 8 via an inspiratory tube 6 and carry away gas from the lungs 8 via an expiratory tube 10. Four optional, pressurized gases can be connected to the ventilator 4 via four gas connectors 12A, 12B, 12C and 12D and mixed in a gas mixer 14 before the mixed breathing gas is sent to the lungs 8. The gas connectors 12A, 12B, 12C and 12D are respectively provided with a flow valve 16A, 16B, 16C and 16D, which regulates the inflow of the respective gas to the gas mixer 14, so that a gas mixture containing exact ratios of the different gases can be obtained. The valves 16A, 16B, 16C and 16D are controlled by a control and analysis device 18 which transmits control signals to the valves 16A, 16B, 16C and 16D via four control signal lines 20A, 20B, 20C and 20D. The gas flow from the gas mixer 14 to the inspiratory tube 6 is controlled by an inspiratory valve 22 so that a desired flow profile is produced. The inspiratory valve 22 is also controlled by the control and analysis device 18 which, via a control signal line 24, sends control signals to the inspiratory valve 22.

The valves 16A, 16B, 16C and 16D are sufficient to control a flow of breathing gas with a desired flow profile. A Servo Ventilator 300, commercially available from Siemens-Elema AB could, for instance, be equipped with a calculation unit and perform the FRC-calculations as in the described embodiment.

In measurement of the lungs functional residual capacity, a gas mixture comprising a predetermined concentration of a trace gas, such as $SF_6$, is supplied. The trace gas must be inert and should not be absorbed by the body. In this manner, the lungs will contain the predetermined concentration of trace gas after a number of respiratory cycles. When trace gas feed is stopped and the concentration of trace gas in gas expired from the lungs is measured until the trace gas has been washed out of the lungs, the functional residual capacity of the lungs can be calculated.

The mixed gas is fed to the lungs 8 via the inspiratory tube 6 and passes a gas meter 26 which measures the concentration of trace gas and sends a measurement signal via a measurement signal line 28 to the control and analysis device 18. During the wash-in phase, i.e. when trace gas is supplied to the lungs, the gas meter 26 measures the concentration both during inspiration and expiration. When the concentration of trace gas is the same during both inspiration and expiration, a state of equilibrium exists in which the lungs contain the, predetermined concentration of trace gas. The gas meter 26 can now be calibrated, since the measurement signal for 0% (before trace gas is added) and the measurement signal for the predetermined concentration are known. This results in more accurate measurement during the washout phase than in conventional techniques wherein the gas meter is calibrated before trace gas is supplied to the lungs.

During expiration, when the gas passes through the expiratory tube 10, the gas passes a flow meter 30 which measures the expired gas flow and sends a measurement signal to the control and analysis device 18 via a measurement signal line 32. Expired gas also passes an expiratory valve 34 which regulates expiratory flow and Positive End Expiratory Pressure (PEEP,). The expiratory valve 34 is controlled by the control and analysis device 18 which, via a control signal line 36, sends control signals to the expiratory valve 34.

Since both expired flow and the concentration of trace gas in the expired flow are measured during the; washout phase, the volume of trace gas which was in the lungs can be measured. Since the concentration of trace gas in the lungs during equilibrium is also known, the volume of the lungs can also be calculated.

Since gas meters generally exhibit signal drift, some form of correction is necessary. In the present embodiment, this correction is achieved in such a way that measurement values during the washout phase are stored in a memory 38 at the same time as a value for signal drift is calculated. This value is calculated by recording the measurement signal at inspiration during the washout phase. The signal can be recorded for each respiratory cycle or at intervals, e.g., every fifth respiratory cycle. No trace gas is supplied during washout, and the concentration is therefore 0%. Any change in the measurement signal must therefore be due to signal drift. Calculation of the volume of trace gas can then be made with correction for the calculated signal drift. Alternatively, the gas meter 26 can be zeroed at inspiration when the washout phase is in progress. At the beginning of the washout phase, the concentration of trace gas is so high that minor drift in the gas meter 26 does not affect the final results very much. After a while, concentration of trace gas during inspiration will become 0%. Zeroing will then be possible.

The fact that the inspiratory tube 6 still contains some trace gas at the beginning of the washout phase and t,he fact that a number of respiratory cycles must occur before the gas meter 14 and the inspiratory tube 6 have been emptied of trace gas must, however, be taken into account.

Another factor to consider is that at the beginning of each inspiration, some residual trace gas is returned to the lungs 8, since part of the gas is re-breathed.

These problems can be overcome relatively simply. When the inspiratory tube 6 has been emptied of trace gas after some respiratory cycles of the washout phase, trace gas will only be present at the onset of each inspiration. By measuring the signal at the end of inspiration, or zeroing the gas meter 26 at the end of inspiration, all re-breathed gas will be in the lungs 8 anti only fresh breathing gas (comprising 0% trace gas) passes the gas meter 26.

Another possibility is to set the null level of the gas meter 26 at the calibrated concentration level. Since the gas meter 26 generates a voltage signal corresponding to the concentration, null can be set at any desired level.

More important, however, is that the volume of re-breathed gas can affect the calculation of the functional residual capacity. The calculated value should therefore be corrected for this re-breathed gas volume. The volume of re-breathed gas at each inspiration is relatively constant and can be estimated. Re-breathed volume can, e.g., depend on the equipment used, such as size of the Y-piece, diameter of tubing, etc. Since the concentration of trace gas in the expiratory gas is known for each respiratory cycle, the volume of re-breathed trace gas can be calculated. Alternatively, the concentration of trace gas and the gas flow can be measured during inspiration, and the volume of re-breathed trace gas can be calculated in this way. This latter method provides a more accurate calculation.

FIG. 2 shows an apparatus 39 which is constructed to perform both embodiments of the method according to the invention. The apparatus 39 is in this specific embodiment intended to be used for spontaneously breathing patients. The apparatus 39 has an open inspiratory tube 40 through which the patient draws in air at inspiration. Air passes a first check valve 42 which keeps inspired air from escaping through the inspiratory tube 40. The air then passes down into a pair of lungs 44. From the lungs 44, the air at expiration passes through an expiratory tube 46 out into ambient air. In the expiratory tube 46 there is a second check valve 48 to prevent re-breathing of gas from the expiratory tube 46. Thus, the check valves 42 and 48 control the flow of air to/from the lungs 44.

In the inspiratory tube 40, a first flow meter 50 is located to measure spontaneous, inspired flow. A measurement signal is sent to a control and analysis device 52. On the basis of the measured flow, the control and analysis device 52 controls the supply of trace gas from a gas source 54. Trace gas is fed to the inspiratory tube 40 through a gas tube 56. A specific concentration of trace gas is thereby supplied to the lungs 44. A gas meter 58 measures the concentration of trace gas both during inspiration and expiration during the wash-in phase and sends the measurement signals to the control and analysis device 52. In the expiratory tube 46, a second flow meter 60 is located to measure spontaneous, expired flow. A measurement signal is sent to the control and analysis device 52.

In this instance, the flow of both inspired and expired air and the concentration of trace gas in inspired and expired air are both measured. During the wash-in phase, both the volume of trace gas supplied and the volume of trace gas carried away can therefore be calculated. The difference between these volumes is the volume of trace gas in the lungs 44. This volume can therefore be calculated directly instead of being determined during the washout phase. FRC can therefore be calculated more rapidly than in known methods.

The volume of re-breathed trace gas is minimal, since the check valves 42 and 48 prevent trace gas from diffusing out into the inspiratory tube 40 and prevent re-breathing of gas from the expiratory tube 46.

The gas meter 58 can be calibrated in the same way as with the ventilator device 2 in FIG. 1. Signal drift during the wash-in phase can be determined with measurements made at a 0% concentration of trace gas before and after the measurement.

Combinations of the described apparatuses are naturally fully possible. Thus, the ventilator device 2 in FIG. 1 can be equipped with a flow meter near the inspiratory tube 6 and FRC determined during the wash-in phase. Further, the ventilator device 2 in FIG. 1 can be used for spontaneously breathing patients as well as for supported and controlled mechanical ventilation of patients. In controlled mechanical ventilation of the patient, inspiratory flow through the inspiratory valve 22 can be controlled so exactly that this flow is always known (less than 0.1% deviation from set flow), and a flow meter is then unnecessary when determining FRC during wash-in. The ventilator device 2 can also be equipped with check valves in the inspiratory and expiratory tubes 6 and 10. As stated above, the apparatus 39 in FIG. 2 can even determine FRC during washout in the same manner as in the description of FIG. 1.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for determining the functional residual capacity of lungs, comprising the steps of:

supplying a predetermined concentration of a trace gas to a breathing gas and feeding said breathing gas with said predetermined concentration of said trace gas into the lungs through a gas meter during a wash-in phase;

measuring the concentration of said trace gas in gas inspired by and expired from the lungs with said gas meter;

stopping the supply of said trace gas when the concentration of said trace gas measured in the expired gas becomes identical to the concentration measured in the inspired gas;

starting a washout phase;

measuring the concentration of said trace gas in the expired gas in said washout phase with said gas meter until the measured concentration falls below a predetermined threshold value;

measuring the flow of expired gas for every respiratory cycle in said washout phase; and at an end of said washout phase, calculating the volume of said trace gas expired during the washout phase from the measured concentration of said trace gas in the expired gas and the measured flow of expired gas, and calculating the functional residual capacity of the lungs by dividing said volume, of said trace gas by said concentration of said trace gas.

2. A method as claimed in claim 1, comprising the additional step of setting said gas meter to a null level for the concentration of said trace gas at said predetermined concentration.

3. A method as claimed in claim 1, comprising the additional steps of:

storing measurement values obtained during the washout phase in a memory;

measuring a signal drift of said gas meter; and correcting the stored measurement values for the measured signal drift before calculating said volume.

4. A method as claimed in claim 1 wherein the step of measuring the concentration of said trace gas in the inspired gas comprises measuring the concentration of said trace gas in the inspired gas during said washout phase followed by measuring a volume of residual trace gas and thereby identifying a re-breathed volume of trace gas, and correcting the calculated volume of trace gas by compensating for said re-breathed volume of trace gas.

5. A method for determining the functional residual capacity of lungs, comprising the steps of:

feeding a breathing gas comprising a predetermined concentration of a trace gas into the lungs through a gas meter during a wash-in phase;

measuring an inspired concentration of said trace gas in gas inspired by the lungs and an expired concentration of said trace gas expired from the lungs with said gas meter during said wash-in phase until the concentration of said trace gas in the inspired gas is the same as the concentration of said trace gas in the expired gas;

measuring an inspired flow of gas for each respiratory cycle in the wash-in phase;

measuring an expired flow of gas for each respiratory cycle in said wash-in phase;

calculating a volume of inspired trace gas in said wash-in phase from the measured inspired concentration of said trace gas and the measured inspired flow of gas and calculating a volume of expired trace gas from the measured expired concentration of said trace gas and the measured expired flow of gas; and calculating a volume of said trace gas in the lungs by subtracting the volume of expired trace gas from the volume of inspired trace gas, and calculating the functional residual capacity of the lungs by dividing said volume of trace gas in the lungs by said expired concentration of said trace gas.

6. An apparatus for ventilating a patient comprising:

ventilator means for supplying breathing gas to and carrying expired gas away from the lungs of said patient;

a gas source, connected to said ventilator means, for supplying a trace gas mixed with said breathing gas to the lungs of said patient during a wash-in phase during the inspiratory phase of a plurality of respiratory cycles until the lungs contain a predetermined concentration of the trace gas;

gas meter means, through which the mixture of said breathing gas and said trace gas passes, for measuring the concentration of said trace gas during the wash-in phase and during a subsequent washout phase in the expiratory phase of said plurality of respiratory cycles until the concentration of said trace gas measured during the washout phase falls below a predetermined threshold value;

flow meter means for measuring expiratory flow during said washout phase; and analyzer means supplied with said measured values for the trace gas concentration and expiratory flow during said washout phase, for determining the volume of trace gas leaving the lungs and, from said volume of trace gas leaving the lungs, determining the functional residual capacity of the lungs.

7. An apparatus as claimed in claim 6 wherein said analyzer means comprises a memory in which measurement values for the concentration of said trace gas and the flow of expired gas are stored during said washout phase.

* * * * *